(12) United States Patent  (10) Patent No.: US 8,749,359 B1
Wilson  (45) Date of Patent: Jun. 10, 2014

(54) TABLET HOLDER WITH ALERT SYSTEM

(76) Inventor: Ruta Wilson, Owen Sound (CA)

( * ) Notice: Subject to any disclaimer, the term of this patent is extended or adjusted under 35 U.S.C. 154(b) by 761 days.

(21) Appl. No.: 12/979,714

(22) Filed: Dec. 28, 2010

(51) Int. Cl.
*G08B 1/00* (2006.01)
*G06Q 50/00* (2012.01)
*G06F 17/00* (2006.01)
*B65H 1/00* (2006.01)

(52) U.S. Cl.
USPC ............... 340/309.16; 340/309.4; 340/568.1; 700/235; 700/231; 700/232; 700/236; 700/244; 705/3

(58) Field of Classification Search
USPC ............ 340/309.16, 568; 700/235, 231, 232, 700/236; 206/534, 538
See application file for complete search history.

(56) References Cited

U.S. PATENT DOCUMENTS

| | | |
|---|---|---|
| 4,473,156 A | 9/1984 | Martin |
| D279,551 S | 7/1985 | Claytor, III |
| 5,099,463 A | 3/1992 | Lloyd et al. |
| 5,200,891 A | 4/1993 | Kehr et al. |
| 5,289,157 A | 2/1994 | Rudick et al. |
| 5,408,443 A | 4/1995 | Weinberger |
| 6,169,707 B1 * | 1/2001 | Newland ................. 368/10 |
| 7,006,893 B2 * | 2/2006 | Hart et al. ............... 700/235 |
| 7,978,564 B2 * | 7/2011 | De La Huerga ......... 368/10 |
| 8,055,380 B1 * | 11/2011 | Verma et al. ............ 700/242 |
| 8,214,077 B2 * | 7/2012 | Bertrand et al. ........ 700/236 |
| 2003/0023345 A1 * | 1/2003 | Depeursinge ........... 700/237 |
| 2007/0093935 A1 * | 4/2007 | Fu .......................... 700/237 |
| 2008/0162192 A1 * | 7/2008 | Vonk et al. .............. 705/3 |
| 2011/0231011 A1 * | 9/2011 | Powers ................... 700/236 |

* cited by examiner

Primary Examiner — Fekadeselassie Girma

(57) ABSTRACT

A tablet holder with an alert system for reminding individuals to take their medications featuring a base with seven compartments. Each compartment has a separate lid, and a base lid covers all the compartment lids. Compartment LEDs are disposed in each compartment lid. A touch screen display, a speaker, a vibrating component, and a microprocessor are each disposed in the base. The microprocessor is connected to a time keeping system that keeps the date and time. The microprocessor can be programmed to be activated at various dates and times. When the microprocessor is activated, the microprocessor activates the LEDs, the speaker, and the vibrating component to alert the user to take his/her medicine.

7 Claims, 5 Drawing Sheets ns on schedule. The present invention features a tablet
TABLET HOLDER WITH ALERT SYSTEM

FIELD OF THE INVENTION

The present invention is directed to a tablet holder for medications and vitamins, more particularly to a tablet holder with an alert system that provides a sound alert, a light alert, and a vibration alert.

BACKGROUND OF THE INVENTION

Many individuals forget to take their medications or vitamins on schedule. The present invention features a tablet holder with an alert system that provides a sound alert, a light alert, and a vibration alert. The multiple means of alerting uses can help ensure that individuals take their medications on time. The sound and light alerts can help those who are visibly or audibly impaired.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY

The present invention features a tablet holder. In some embodiments, the table holder comprises an elongated base having seven compartments, each compartment is adapted to hold a pill; seven compartment lids pivotally attached to a top side edge of the base via a hinge, wherein each compartment lid covers a compartment, the compartment lids can each pivot between at least an open position and a closed position respectively allowing and preventing access to the respective compartment; a base lid pivotally attached to the base on the top side edge via the hinge, the base lid functions to cover the compartment lids, the base lid can pivot between at least an open position and a closed position respectively allowing and preventing access to the compartment lids; a compartment light emitting diode (LED) disposed in each compartment lid, the compartment LEDs are visible from top surfaces of the compartment lids, each compartment LED is operatively connected to a power source; a display disposed on the base lid, the display is a touch screen display; a speaker and a vibrating component each disposed in the base lid, the speaker is adapted to emit an audible sound when activated and the vibrating component is adapted to vibrate when activated; and a microprocessor disposed in the base lid, the microprocessor is operatively connected to each compartment LED, the display, the speaker, and the vibrating component, the microprocessor is operatively connected to a standard time keeping system which is adapted to keep a date and a time in a standard manner, the microprocessor is adapted to be programmed via the display to be activated on certain days and times, the microprocessor is adapted to save information via memory.

When the microprocessor is activated the microprocessor sends (i) a first output command to the compartment LEDs to cause the compartment LEDs to be illuminated; (ii) a second output command to the speaker to cause the speaker to emit the audible sound; and (iii) a third output command to the vibrating component to cause the vibrating component to vibrate.

In some embodiments, one or more compartments are divided into sub-compartments. In some embodiments, the power source is a battery. In some embodiments, the battery is a rechargeable battery. In some embodiments, the display is disposed on an inner surface of the base lid. In some embodiments, the memory is flash memory, random access memory, or read only memory.

In some embodiments, tablet holder further comprises a holding unit, an inner chamber is disposed in the holding unit adapted to hold a side end of the base, and the holding unit comprises a plug adapted to operatively connect to an electrical outlet. In some embodiments, the holding unit further comprises second electrical contacts operatively connected to the plug and the base further comprises first electrical contacts operatively connected to the power source and to the microprocessor, the second electrical contacts engage the first electrical contacts when the base is engaged in the holding unit to recharge the power source.

In some embodiments, the holding unit comprises a holding unit display, the holding unit display is a touch screen display and is adapted to program the microprocessor when the base is engaged in the holding unit. In some embodiments, the holding unit further comprises a holding unit speaker adapted to emit an audible sound, wherein when the base is engaged in the holding unit and the microprocessor is activated the microprocessor sends a fourth output signal to the holding unit speaker to activate the holding unit speaker to cause the holding unit speaker to emit the audible sound.

In some embodiments, the holding unit comprises a locator button, the locator button is operatively connected to a transmitter disposed in the holding unit, the transmitter is adapted to communicate with a receiver disposed in the base lid, the receiver is operatively connected to the microprocessor, wherein when the locator button is pressed the locator button activates the transmitter to send a first transmitter signal to the receiver, wherein when the receiver receives the first transmitter signal the receiver sends a first locator input signal to the microprocessor whereupon the microprocessor sends a locator output command to each the speaker, the compartment LEDs, and the vibrator component to activate the speaker, the compartment LEDs, and the vibrator component.

DESCRIPTION OF PREFERRED EMBODIMENTS

Figure 1:
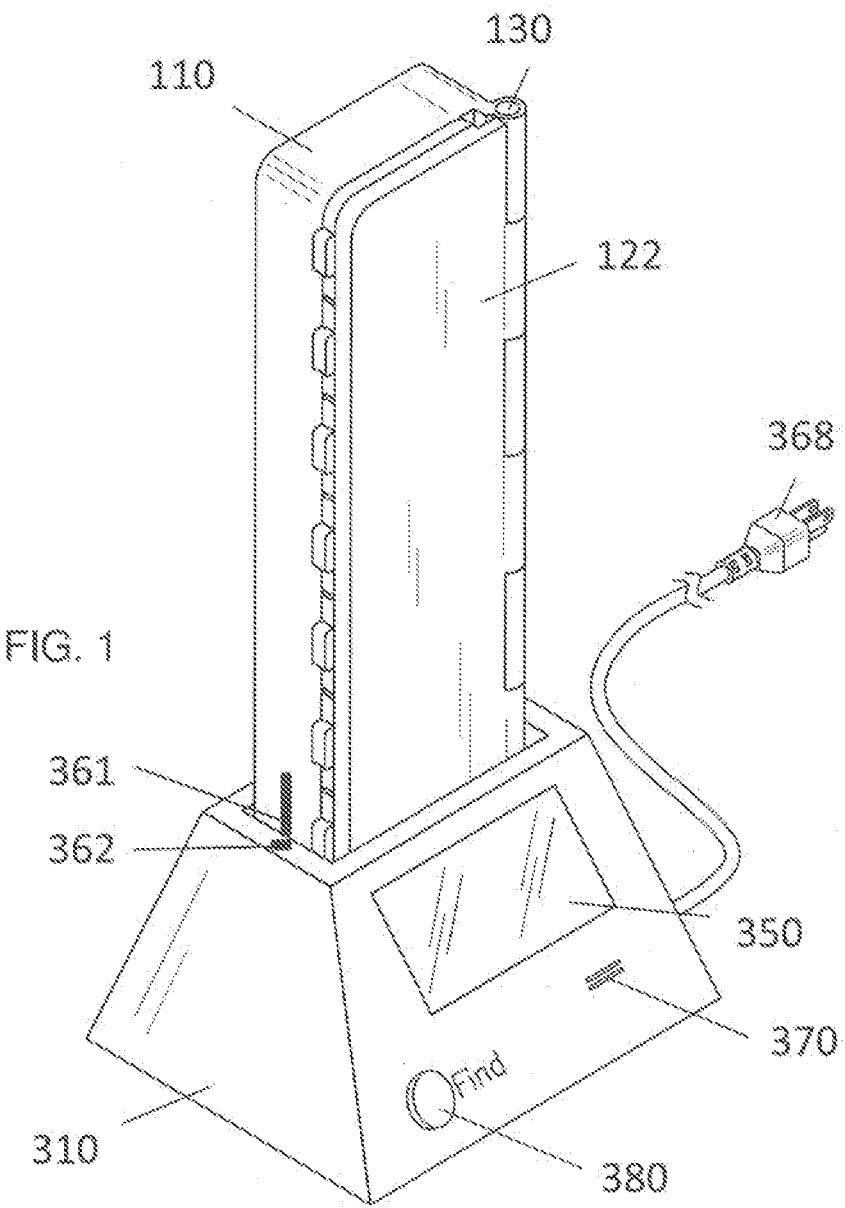
FIG. 1 is a perspective view of the tablet holder of the present invention.
Figure 2:
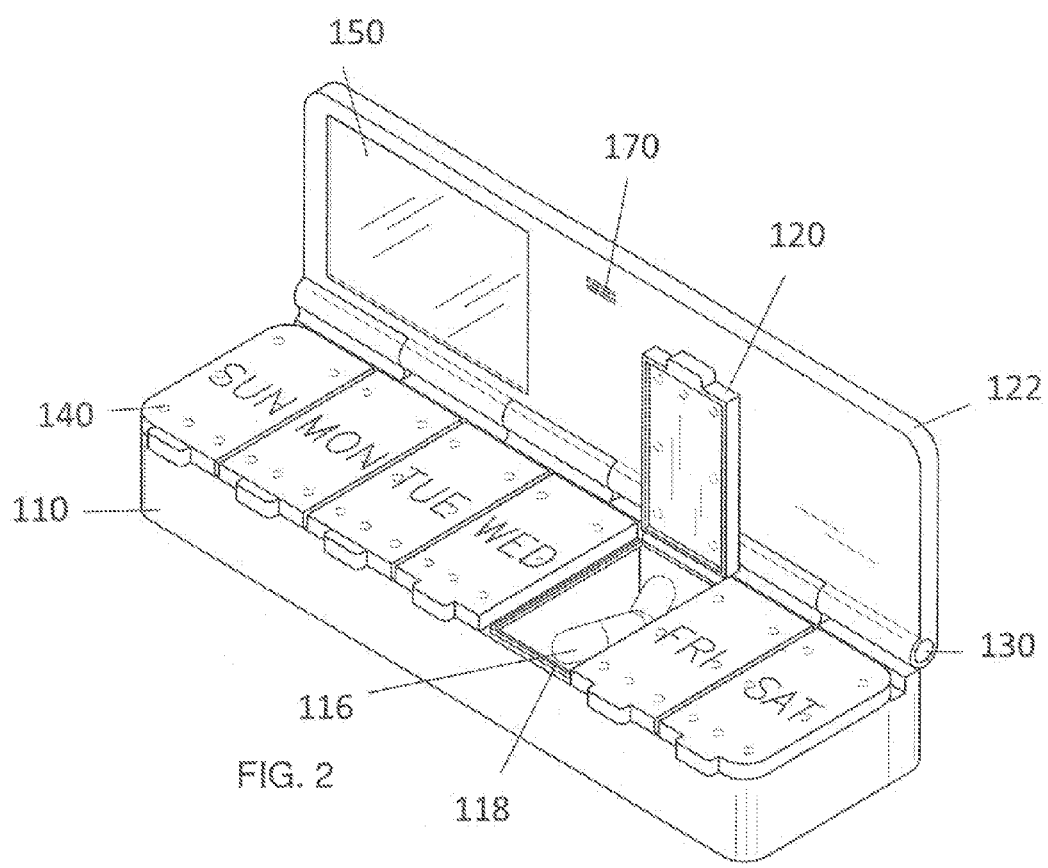
FIG. 2 is a perspective view of the tablet holder of the present invention.
Figure 3:
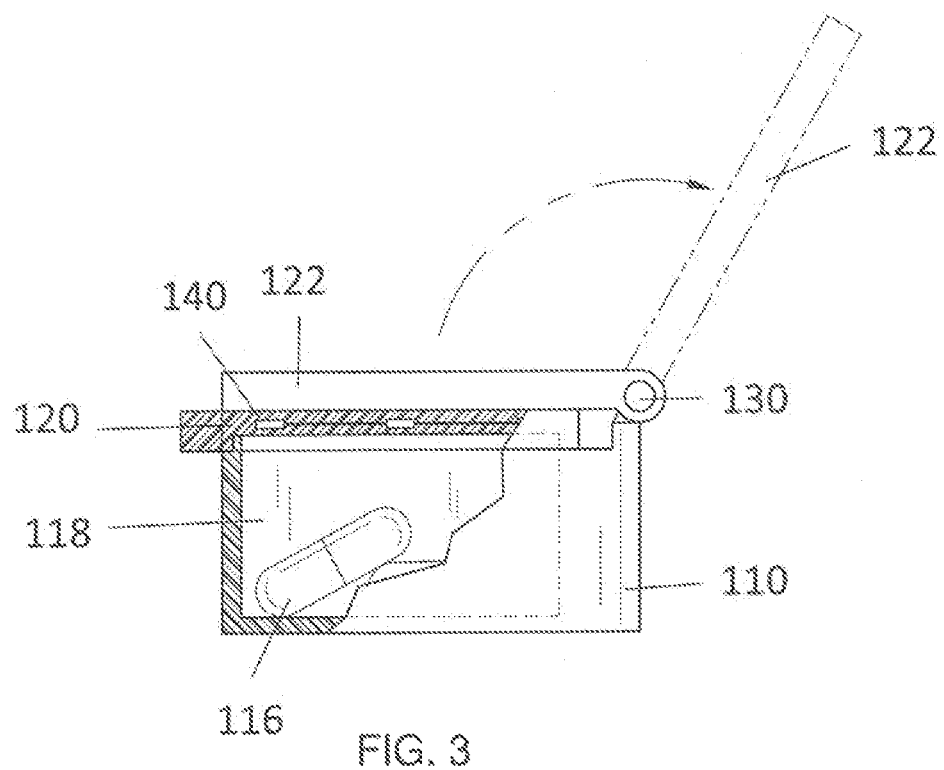
FIG. 3 is a side view of the tablet holder of the present invention.
Figure 4:
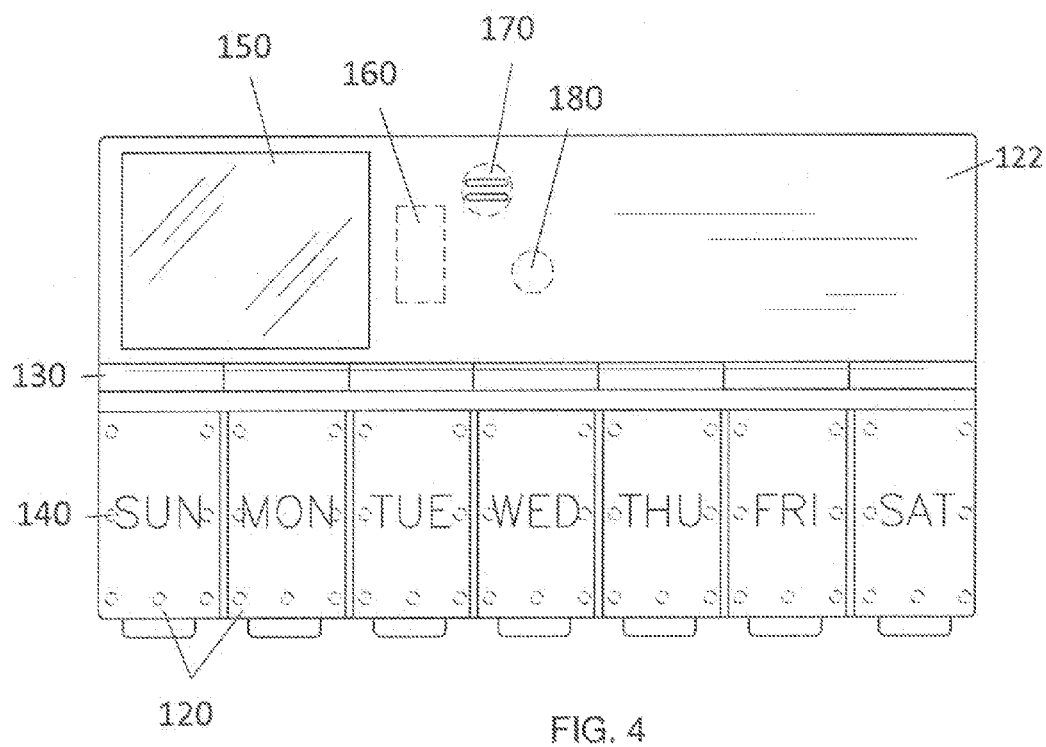
FIG. 4 is a top view of the tablet holder of the present invention.

Referring now to FIG. 1-5, the present invention features a tablet holder with an alert system that provides a sound alert, a light alert, and a vibration alert. The multiple means of alerting uses can help ensure that individuals take their medications on time. The sound and light alerts can help those who are visibly or audibly impaired.

The tablet holder 100 comprises an elongated base 110 having seven compartments 118 (e.g., a first compartment, a second compartment, a third compartment, a fourth compartment, a fifth compartment, a sixth compartment, and a seventh compartment), one for each day of the week. The compartments 118 are adapted to hold pills 116 (e.g., medication, vitamins). In some embodiments, each compartment 118 is divided into sub-compartments (e.g., via compartment walls).

Seven compartment lids 120 (e.g., a first compartment lid, a second compartment lid, a third compartment lid, a fourth compartment lid, a fifth compartment lid, a sixth compartment lid, and a seventh compartment lid) are pivotally attached to the base 110 (e.g., on a top side edge) via a hinge 130, wherein each compartment lid 120 covers a compartment 118. The compartment lids 120 can each pivot between at least an open position and a closed position respectively allowing and preventing access to the respective compartment 118. A base lid 122 is pivotally attached to the base 110 (e.g., on the same top side edge as the compartment lids 120) via the hinge 130. The base lid 122 functions to cover the compartment lids 120 (e.g., see FIG. 2). The base lid 122 can pivot between at least an open position and a closed position respectively allowing and preventing access to the compartment lids 120.

Disposed in each compartment lid 120 is a compartment light emitting diode (LED) 140. The compartment LED 140 is visible from the top surface of the respective compartment lid 120. Each compartment LED is operatively connected to a power source (e.g., a battery, e.g., a rechargeable battery).

Disposed in the base lid 122 is a microprocessor 160. The microprocessor 160 is operatively connected to each compartment LED 140. A display 150 is disposed on the base lid 122 (e.g., on the inner surface 122a of the base lid 122). The display 150 may be a touch screen display. Such touch screen displays are well known to one of ordinary skill in the art. The display 150 is operatively connected to the microprocessor 160. Also disposed in the base lid 122 is a speaker 170. The speaker 170 is operatively connected to the microprocessor 160. In some embodiments, a vibrating component 180 (e.g., a vibrator) is disposed in the base lid 122. The vibrating component 180 is operatively connected to the microprocessor 160. The speaker 170 is adapted to emit an audible sound (e.g., an alarm sound) when activated. The vibrating component 180 is adapted to vibrate when activated.

The microprocessor 160 is operatively connected to a time keeping system 160a, which is adapted to keep the date and time. The microprocessor 160 is adapted to be programmed and save information (e.g., via flash memory, random access memory, read only memory, etc.). For example, a user can program the microprocessor 160 by setting the date and time, and further setting the dates and times he/she should take his/her medicine. Such date and time programming (and using a touch screen to program the microprocessor 160) is well known to one of ordinary skill in the art. For example, a user can program the time keeping system 160a with the current date and time. Next, a user can program the microprocessor 160 to be activated (thus activating the speaker 170 and/or vibrating component 180 and/or compartment LEDs 140) at certain times on certain days (e.g., 8:00 AM every Monday, Wednesday, and Friday; 12:00 PM every day; 6:00 PM every other day, etc.).

When the microprocessor 160 is activated, the microprocessor 160 sends a first output command to the compartment LEDs 140 to cause the compartment LEDs 140 to be illuminated. In some embodiments, the microprocessor 160 send the first output command to the appropriate compartment LED 140 of the compartment that needs to be opened (e.g., if the day is Monday, the compartment LED 140 of the compartment corresponding to Monday is illuminated).

When the microprocessor 160 is activated, the microprocessor 160 sends a second output command to the speaker 170 to cause the speaker 170 to emit the audible sound (e.g., alarm sound). When the microprocessor 160 is activated, the microprocessor 160 sends a third output command to the vibrating component 180 to cause the vibrating component 180 to vibrate.

In some embodiments, the display 150 is adapted to display a message when the battery is low, indicating that the battery should be changed. For example, the holder 100 of the present invention may have a battery indicator. Or, the display 150 may display the battery indicator.

As shown in FIG. 1, in some embodiments, the holder 100 of the present invention further comprises a holding unit 310 adapted to hold the base 110. For example, an inner chamber is disposed in the holding unit 310 adapted to hold the side end of the base 110 (e.g., see FIG. 1). The remaining portion of the base 110 protrudes from the holding unit 310. When the base 110 is engaged in the holding unit 310, the base 110 operatively connects to the holding unit 310 (e.g., first electrical contacts 361 disposed on the base 110 operatively connect to second electrical contacts 362 disposed on the holding unit 310). This can allow for recharging of the battery in the base 110. The holding unit 310 comprises a plug 386 adapted to operatively connect to an electrical outlet in a standard manner.

A holding unit display 350 is disposed on the holding unit 310. The holding unit display 350 may be a touch screen display, which is well known to one of ordinary skill in the art. The holding unit display 350 may be used in the same manner as the display 150 on the base lid 122 to program the microprocessor 160. In some embodiments, a holding unit speaker 370 is disposed on the holding unit 310. The holding unit speaker 370 is adapted to emit an audible sound (e.g., an alert sound). In some embodiments, when the base 110 is engaged in the holding unit 310 and the microprocessor 160 is activated (e.g., when it's time for the user to take his/her medication), the microprocessor 160 sends a fourth output signal to the holding unit speaker 370 to activate the holding unit speaker 370 to cause the holding unit speaker 370 to emit an audible sound (e.g., alarm).

Figure 5:
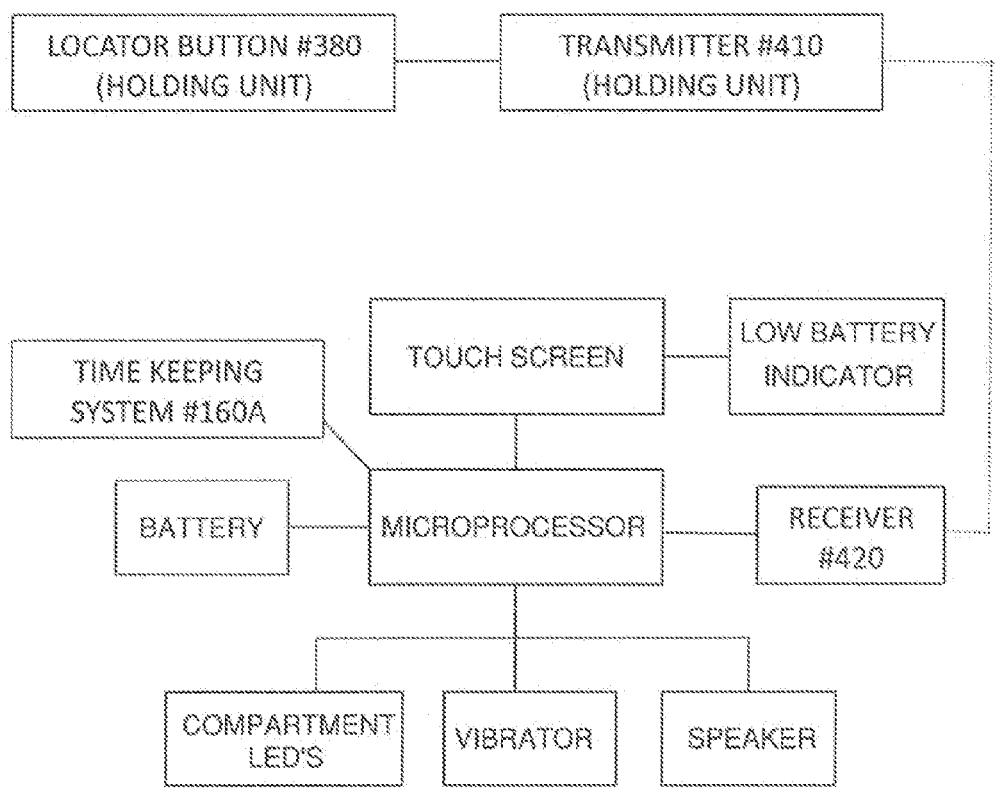
FIG. 5 is a schematic view of the electrical components of the tablet holder of the present invention.

As shown in FIG. 1 and FIG. 5, in some embodiments, the holding unit 310 comprises a locator button 380. The locator button 380 is operatively connected to a transmitter 410, which is adapted to communicate with a receiver 420 disposed in the base 110 or base lid 122 (the receiver being operatively connected to the microprocessor 160). When the locator button 380 is pressed, the locator button 380 activates the transmitter 410 to send a first transmitter signal to the receiver 420. Upon receipt of the first transmitter signal, the receiver 420 sends a first locator input signal to the microprocessor 160 whereupon the microprocessor 160 sends a locator output command to each the speaker 170, the compartment LEDs 140, and the vibrator component 180 to activate the speaker 170, the compartment LEDs 140, and the vibrator component 180. This can help a user locate the base 110 if it is lost.

In some embodiments, the tablet holder 100 is capable of recording a user's (patient's identity), for example in case the tablet holder 100 is lost. The audio, light, and vibration functions of the base 110 and/or holding unit 310 may be programmable.

The disclosures of the following U.S. Patents are incorporated in their entirety by reference herein: U.S. Pat. No. 6,169,707; U.S. Pat. No. 5,099,463; U.S. Pat. No. 4,473,156; U.S. Pat. No. 5,408,443; U.S. Pat. No. 5,289,157; U.S. Pat. No. 5,200,891; U.S. Design Pat. No. D279,551.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

The reference numbers recited in the below claims are solely for ease of examination of this patent application, and are exemplary, and are not intended in any way to limit the scope of the claims to the particular features having the corresponding reference numbers in the drawings.

What is claimed is:

1. A tablet holder comprising:
   (a) an elongated base 110 having seven compartments 118, each compartment 118 holds a pill 116;
   (b) seven compartment lids 120 pivotally attached to a top side edge of the base 110 via a hinge 130, wherein each compartment lid 120 covers a compartment 118, the compartment lids 120 can each pivot between at least an open position and a closed position respectively allowing and preventing access to the respective compartment 118;
   (c) a base lid 122 pivotally attached to the base 110 on the top side edge via the hinge 130, the base lid 122 functions to cover the compartment lids 120, the base lid 122 can pivot between at least an open position and a closed position respectively allowing and preventing access to the compartment lids 120;
   (d) a compartment light emitting diode (LED) 140 disposed in each compartment lid 120, the compartment LED 140s are visible from top surfaces of the compartment lids 120, each compartment LED is operatively connected to a power source;
   (e) a display 150 disposed on the base lid 122, the display 150 is a touch screen display;
   (f) a speaker 170 and a vibrating component 180 each disposed in the base lid 122, the speaker 170 emits an audible sound when activated and the vibrating component 180 vibrates when activated; and
   (g) a microprocessor 160 disposed in the base lid 122, the microprocessor 160 is operatively connected to each compartment LED 140, the display 150, the speaker 170, and the vibrating component 180, the microprocessor 160 is operatively connected to a standard time keeping system 160a which keeps a date and a time in a standard manner, the microprocessor 160 is programmed via the display 150 to be activated on certain days and times, the microprocessor 160 saves information via memory;
   wherein when the microprocessor 160 is activated the microprocessor 160 sends (i) a first output command to the compartment LEDs 140 to cause the compartment LEDs 140 to be illuminated; (ii) a second output command to the speaker 170 to cause the speaker 170 to emit the audible sound; and (iii) a third output command to the vibrating component 180 to cause the vibrating component 180 to vibrate, and
   (h) a holding unit 310, an inner chamber is disposed in the holding unit 310 holds a side end of the base 110, and the holding unit 310 comprises a plug 386 to operatively connect to an electrical outlet,
   wherein the holding unit 310 further comprises second electrical contacts 362 operatively connected to the plug 386 and the base 110 further comprises first electrical contacts 361 operatively connected to the power source and to the microprocessor 160, the second electrical contacts 362 engage the first electrical contacts 361 when the base 110 is engaged in the holding unit 310 to recharge the power source,
   wherein the holding unit 310 further comprises a holding unit speaker 370 which emits an audible sound, wherein when the base 110 is engaged in the holding unit 310 and the microprocessor 160 is activated the microprocessor 160 sends a fourth output signal to the holding unit speaker 370 to activate the holding unit speaker 370 to cause the holding unit speaker 370 to emit the audible sound
   wherein the holding unit 310 further comprises a holding unit display 350, the holding unit display 350 is a touch screen display and programs the microprocessor 160 when the base 110 is engaged in the holding unit 310
   wherein the holding unit 310 further comprises a locator button 380, the locator button 380 is operatively connected to a transmitter 410 disposed in the holding unit 310, the transmitter 410 communicates with a receiver 420 disposed in the base lid 122, the receiver 420 is operatively connected to the microprocessor 160, wherein when the locator button 380 is pressed the locator button 380 activates the transmitter 410 to send a first transmitter signal to the receiver 420, wherein when the receiver 420 receives the first transmitter signal the receiver 420 sends a first locator input signal to the microprocessor 160 whereupon the microprocessor 160 sends a locator output command to each the speaker 170, the compartment LEDs 140, and the vibrator component 180 to activate the speaker 170, the compartment LEDs 140, and the vibrator component 180.

2. The tablet holder of claim 1, wherein a compartment 118 is divided into sub-compartments.

3. The tablet holder of claim 1, wherein the power source is a battery.

4. The tablet holder of claim 3, wherein the battery is a rechargeable battery.

5. The tablet holder of claim 1, wherein the display 150 is disposed on an inner surface 122a of the base lid 122.

6. The tablet holder of claim 1, wherein the memory is flash memory, random access memory, or read only memory.

7. A tablet holder consisting of:
   (a) an elongated base 110 having seven compartments 118, each compartment 118 holds a pill 116;
   (b) seven compartment lids 120 pivotally attached to a top side edge of the base 110 via a hinge 130, wherein each compartment lid 120 covers a compartment 118, the compartment lids 120 can each pivot between at least an open position and a closed position respectively allowing and preventing access to the respective compartment 118;
   (c) a base lid 122 pivotally attached to the base 110 on the top side edge via the hinge 130, the base lid 122 functions to cover the compartment lids 120, the base lid 122 can pivot between at least an open position and a closed position respectively allowing and preventing access to the compartment lids 120;
   (d) a compartment light emitting diode (LED) 140 disposed in each compartment lid 120, the compartment LED 140s are visible from top surfaces of the compartment lids 120, each compartment LED is operatively connected to a power source;
   (e) a display 150 disposed on the base lid 122, the display 150 is a touch screen display;

(f) a speaker 170 and a vibrating component 180 each disposed in the base lid 122, the speaker 170 emits an audible sound when activated and the vibrating component 180 vibrates when activated; and (g) a microprocessor 160 disposed in the base lid 122, the microprocessor 160 is operatively connected to each compartment LED 140, the display 150, the speaker 170, and the vibrating component 180, the microprocessor 160 is operatively connected to a standard time keeping system 160*a* which keeps a date and a time in a standard manner, the microprocessor 160 is programmed via the display 150 to be activated on certain days and times, the microprocessor 160 saves information via memory;

wherein when the microprocessor 160 is activated the microprocessor 160 sends (i) a first output command to the compartment LEDs 140 to cause the compartment LEDs 140 to be illuminated; (ii) a second output command to the speaker 170 to cause the speaker 170 to emit the audible sound; and (iii) a third output command to the vibrating component 180 to cause the vibrating component 180 to vibrate, (h) a holding unit 310, an inner chamber is disposed in the holding unit 310 holds a side end of the base 110, and the holding unit 310 comprises a plug 386 to operatively connect to an electrical outlet, wherein the holding unit 310 further consists of second electrical contacts 362 operatively connected to the plug 386 and the base 110 further comprises first electrical contacts 361 operatively connected to the power source and to the microprocessor 160, the second electrical contacts 362 engage the first electrical contacts 361 when the base 110 is engaged in the holding unit 310 to recharge the power source, wherein the holding unit 310 further consists of a holding unit speaker 370 to emit an audible sound, wherein when the base 110 is engaged in the holding unit 310 and the microprocessor 160 is activated the microprocessor 160 sends a fourth output signal to the holding unit speaker 370 to activate the holding unit speaker 370 to cause the holding unit speaker 370 to emit the audible sound, wherein the holding unit 310 further consists of a holding unit display 350, the holding unit display 350 is a touch screen display and programs the microprocessor 160 when the base 110 is engaged in the holding unit 310, wherein the holding unit 310 further consists of a locator button 380, the locator button 380 is operatively connected to a transmitter 410 disposed in the holding unit 310, the transmitter 410 communicates with a receiver 420 disposed in the base lid 122, the receiver 420 is operatively connected to the microprocessor 160, wherein when the locator button 380 is pressed the locator button 380 activates the transmitter 410 to send a first transmitter signal to the receiver 420, wherein when the receiver 420 receives the first transmitter signal the receiver 420 sends a first locator input signal to the microprocessor 160 whereupon the microprocessor 160 sends a locator output command to each the speaker 170, the compartment LEDs 140, and the vibrator component 180 to activate the speaker 170, the compartment LEDs 140, and the vibrator component 180.

* * * * *